(12) United States Patent
Huthmacher

(10) Patent No.: US 10,463,808 B2
(45) Date of Patent: Nov. 5, 2019

(54) MEDICAMENT DELIVERY DEVICE

(71) Applicant: Sanofi-Aventis Deutschland GMBH, Frankfurt am Main (DE)

(72) Inventor: Winfried Huthmacher, Frankfurt (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 393 days.

(21) Appl. No.: 15/111,964

(22) PCT Filed: Jan. 27, 2015

(86) PCT No.: PCT/EP2015/051595
§ 371 (c)(1),
(2) Date: Jul. 15, 2016

(87) PCT Pub. No.: WO2015/113969
PCT Pub. Date: Aug. 6, 2015

(65) Prior Publication Data
US 2016/0339182 A1 Nov. 24, 2016

(30) Foreign Application Priority Data

Jan. 30, 2014 (EP) .................................... 14153203

(51) Int. Cl.
*A61M 5/32* (2006.01)
*A61M 5/315* (2006.01)

(52) U.S. Cl.
CPC ........ *A61M 5/326* (2013.01); *A61M 5/31511* (2013.01); *A61M 5/3287* (2013.01); *A61M 2005/3247* (2013.01); *A61M 2005/3267* (2013.01)

(58) Field of Classification Search
CPC .......... A61M 5/326; A61M 2005/3261; A61M 2005/3265; A61M 5/2429; A61M 5/2425; A61M 2005/3267
See application file for complete search history.

(56) References Cited

U.S. PATENT DOCUMENTS

2012/0101446 A1 4/2012 Heald
2013/0324923 A1* 12/2013 Roberts ................. A61M 5/326
604/110

FOREIGN PATENT DOCUMENTS

| CN | 101282752 | 10/2008 |
| CN | 103079612 | 5/2013 |
| CN | 103442751 | 12/2013 |

(Continued)

OTHER PUBLICATIONS

International Search Report and Written Opinion in International Application No. PCT/EP2015/051595, dated Jun. 5, 2015, 11 pages.

(Continued)

*Primary Examiner* — Nathan R Price
*Assistant Examiner* — Melissa A Snyder
(74) *Attorney, Agent, or Firm* — Fish & Richardson P.C.

(57) ABSTRACT

Described is a medicament delivery device (1), comprising a piston rod (11), and a container carrier (7) for retaining a medicament container, such as a syringe (8), within the body (2). At least one longitudinal rib (2.2) associated with the piston rod (11) is arranged to engage the carrier (7). At least one of the carrier (7) and the at least one rib (2.2) comprises a resilient material adapted to be deformed by the engagement between the carrier (7) and the at least one rib (2.2).

20 Claims, 7 Drawing Sheets

(56) References Cited

FOREIGN PATENT DOCUMENTS

| JP | 2012-519514 | 8/2012 |
| JP | 2013-529986 | 7/2013 |
| WO | WO2007/020090 | 2/2007 |
| WO | WO2007/047200 | 4/2007 |
| WO | WO 2010/100246 | 9/2010 |
| WO | WO2012/000833 | 1/2012 |
| WO | WO 2012/000835 | 1/2012 |
| WO | WO2012/000837 | 1/2012 |
| WO | WO2012/093072 | 7/2012 |

OTHER PUBLICATIONS

International Preliminary Report on Patentability in International Application No. PCT/EP2015/051595, dated Aug. 2, 2016, 8 pages.
Rote Liste, "50. Hypophysen-, Hypothalamushormone, andere regulatorische Peptide u. ihre Hemmstoffe," Chapter 50, ed. 2008, 20 pages.

* cited by examiner

MEDICAMENT DELIVERY DEVICE

CROSS-REFERENCE TO RELATED APPLICATIONS

This application is a U.S. national stage application under 35 USC § 371 of International Application No. PCT/EP2015/051595, filed on Jan. 27, 2015, which claims priority to European Patent Application No. 14153203.6, filed on Jan. 30, 2014, the entire contents of which are incorporated herein by reference.

TECHNICAL FIELD

The invention relates to a medicament delivery device.

BACKGROUND OF THE INVENTION

Administering an injection is a process which presents a number of risks and challenges for users and healthcare professionals, both mental and physical. Pre-filled syringes that are filled with a selected dosage of a medicament for administering the medicament to a patient are known in the art. Medicament delivery devices comprising a needle sleeve for covering a needle of a pre-filled syringe before and after use are also known. Typically, the needle sleeve is either manually moved or moved by the action of a relaxing spring to surround the needle.

There remains a need for an improved medicament delivery device.

SUMMARY OF THE INVENTION

Certain aspects of the present invention relate to an improved medicament delivery device.

In an exemplary embodiment, a medicament delivery device according to the present invention comprises a piston rod and a container carrier for retaining a medicament container within the body. At least one longitudinal rib associated with the piston rod is arranged to engage the carrier. At least one of the carrier and the at least one rib comprises a resilient material adapted to be deformed by the engagement between the carrier and the at least one rib.

In an exemplary embodiment, the medicament delivery device further comprises a body. The container carrier is arranged within the body. The piston rod is connected to the body, and the at least one rib is arranged within the body in a manner to protrude in a radial inward direction. The carrier is movable from an initial position in a proximal direction relative to the body.

In an exemplary embodiment, the medicament delivery device further comprises a sleeve movable within the body along a longitudinal axis so as to cover or expose an injection needle.

In an exemplary embodiment, the container carrier comprises a transverse portion adapted to support a flange on a syringe barrel of a syringe such that the syringe is prevented from moving in a distal direction relative to the carrier. The transverse portion is attached to a ring shaped collar adapted to engage the at least one rib. The collar has a substantially circular cross section when relaxed, and an internal diameter of the collar is greater than a maximum external diameter of the flange of the syringe. The transverse portion comprises an inner collar connected to first sections of the collar by a number of connecting ribs. The inner collar has an internal diameter substantially corresponding to an external diameter of the syringe barrel. On axial movement of the collar relative to the inner collar the connecting ribs are adapted to tilt the first sections with respect to the longitudinal axis. One or more carrier ribs are arranged on an inner surface of the collar and protrude in a radial inward direction in a manner to engage the flange on the syringe barrel for restricting movement of the syringe in the proximal direction relative to the carrier. The carrier rib comprises a proximal ramp.

In an exemplary embodiment, the rib comprises a step adapted to allow the carrier being moved until proximally abutting the step without being deformed or with a lower extent of deformation and adapted to deform the carrier to a greater extent proximally from the step. A sleeve spring is arranged between the carrier and the sleeve in a manner biasing the sleeve (6) in the distal direction relative to the carrier.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
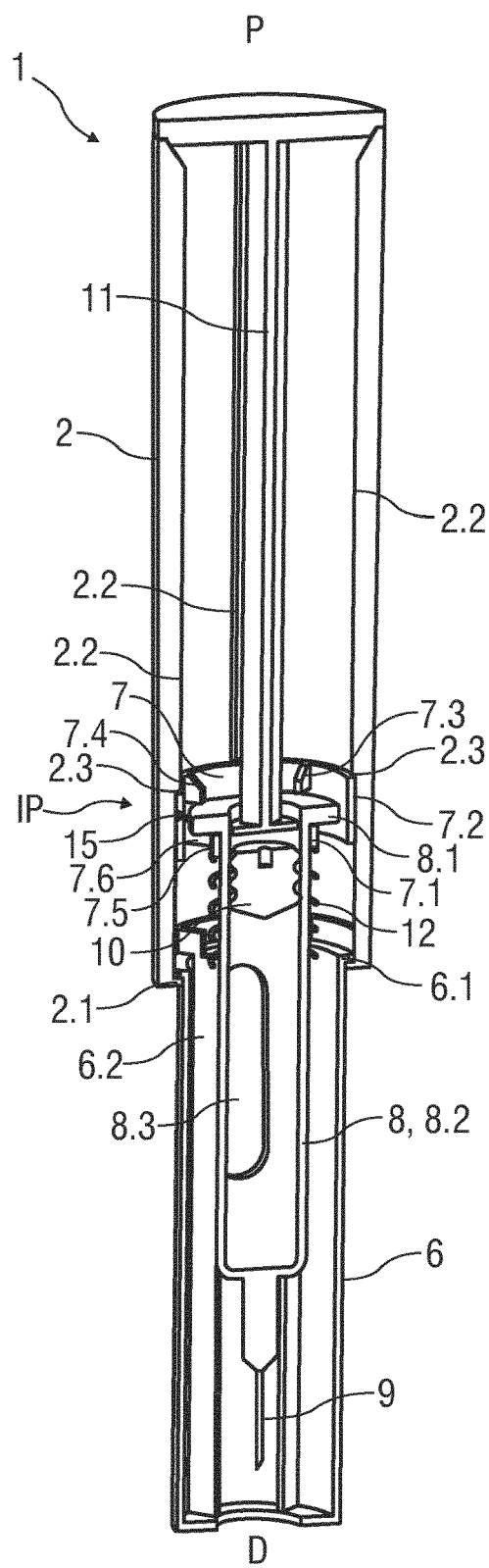
FIG. 1A is a schematic longitudinal section of an exemplary embodiment of a medicament delivery device according to the present invention before use.

FIG. 1A is a schematic longitudinal section of an exemplary embodiment of a medicament delivery device 1 according to the present invention. The medicament delivery device 1 comprises a substantially elongate and cylindrical body 2.

The medicament delivery device 1 furthermore comprises a sleeve 6 with a proximal collar 6.1 and one or more longitudinal ribs 6.2 adapted to center a medicament container within the sleeve 6. The sleeve 6 is slidably coupled to the body 2 for allowing relative movement along a longitudinal axis in a distal direction D and/or a proximal direction P.

A container carrier 7 for retaining a medicament container (e.g., a syringe 8) is arranged within the body 2.

Figure 1B:
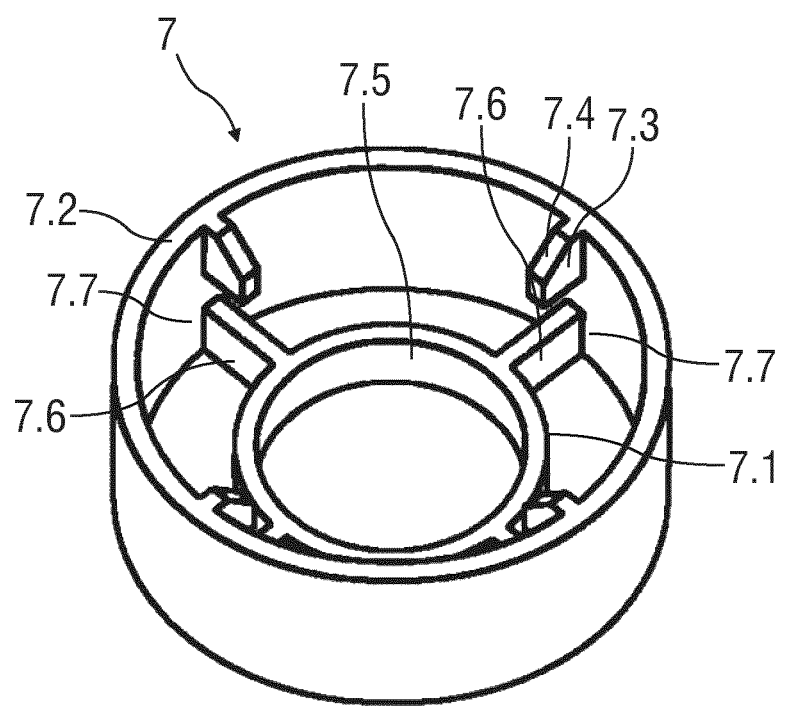
FIG. 1B is a schematic perspective view of an exemplary embodiment of a container carrier according to the present invention.

FIG. 1B is a schematic perspective view of an exemplary embodiment of a container carrier 7.

In an exemplary embodiment, the carrier 7 comprises a resilient material, e.g. a plastic, allowing the carrier 7 to be deformed. In an exemplary embodiment, the container carrier 7 comprises a transverse portion 7.1 adapted to support a flange 8.1 on a syringe barrel 8.2 of the syringe 8 such that the syringe 8 is prevented from moving in the distal direction D relative to the carrier 7. The carrier 7 is slidably disposed within the body 2. The carrier 7 further comprises a collar 7.2 coupled to the transverse portion 7.1. One or more carrier ribs 7.3 are arranged on an inner radial surface of the collar 7.2 and protrude in a radial inward direction in a manner to engage the flange 8.1 on the syringe barrel 8.2 for restricting movement of the syringe 8 in the proximal direction P relative to the carrier 7. The carrier ribs 7.3 may be uniformly distributed over the circumference of the collar 7.2. For example, four carrier ribs 7.3 may be arranged angularly spaced from each other by 90 degrees, respectively. Different numbers of carrier ribs 7.3 with a uniform or non-uniform distribution may likewise be arranged. The collar 7.2 may have a substantially circular cross section with an internal diameter greater than a maximum external diameter of the flange 8.1 of the syringe 8, i.e. a substantially ring shaped clearance 15 is provided between the collar 7.2 and the flange 8.1 allowing for a certain extent of deformation of the collar 7.2.

In an exemplary embodiment, the carrier ribs 7.3 comprise proximal ramps 7.4 adapted to facilitate radial outward deflection of the carrier ribs 7.3 by the flange 8.1 when assembling a syringe 8 to the carrier 7.

In the illustrated embodiment, the transverse portion 7.1 comprises an inner collar 7.5 connected to first sections 7.7 of the collar 7.2 by a number of connecting ribs 7.6. The first sections 7.7 are separated by second sections 7.8 which are not connected to connecting ribs 7.6. In an exemplary embodiment the connecting ribs 7.6 are angularly aligned with the carrier ribs 7.3. The inner collar 7.5 has an internal diameter substantially corresponding to an external diameter of the syringe barrel 8.2. In another exemplary embodiment, the transverse portion 7.1 could be arranged as a transverse disk connected to the collar 7.2. Likewise, the connecting ribs 7.6 may not be aligned with the carrier ribs 7.3 or the numbers of connecting ribs 7.6 may be different from the number of carrier ribs 7.3.

Figure 3:
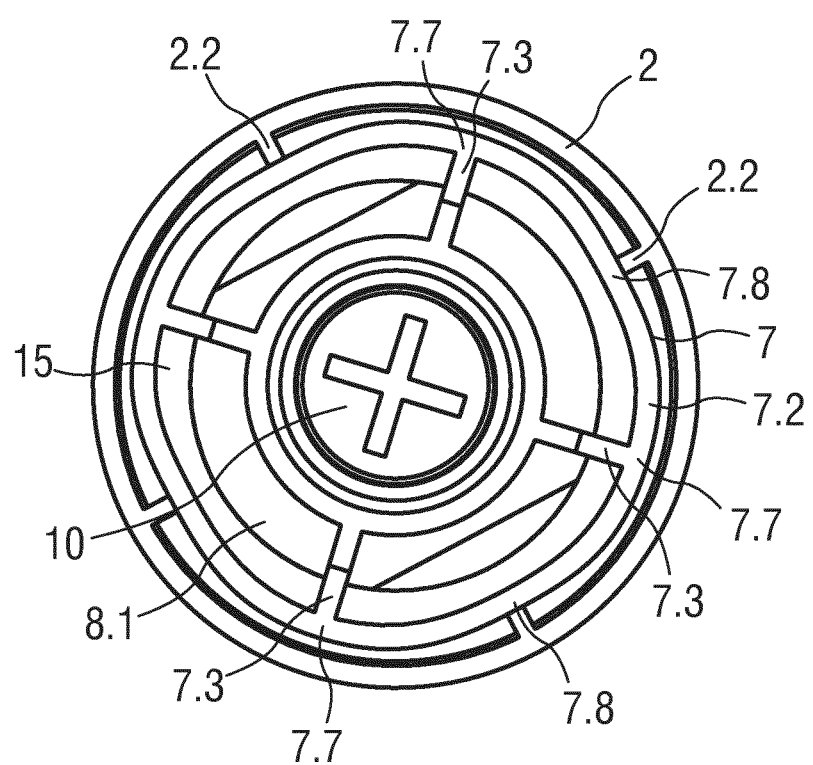
FIG. 3 is a schematic cross sectional view of an exemplary embodiment of a medicament delivery device according to the present invention.

Referring again to FIG. 1A the body 2 comprises one or more longitudinal body ribs 2.2 adapted to radially outwardly abut the collar 7.2 of the carrier 7. When the body ribs 2.2 abut the collar 7.2, the collar 7.2 may be deformed by the body ribs 2.2 such that the collar's 7.2 cross section is no longer circular (as shown in FIG. 3). In an exemplary embodiment, the number of the body ribs 2.2 equals the number of carrier ribs 7.3 and/or connecting ribs 7.6, wherein the carrier 7 is arranged within the body 2 such that the carrier ribs 7.3 and/or connecting ribs 7.6 are angularly offset from the body ribs 2.2. In an exemplary embodiment the carrier ribs 7.3 and/or connecting ribs 7.6 may be equally spaced from the neighbouring body ribs 2.2 (cf. FIG. 3). For example, the carrier 7 may be splined to the body 2 in such a manner that the carrier 7 is in a defined angular position relative to the body 2. The body ribs 2.2 respectively comprise a step 2.3, wherein the internal diameter defined by the body ribs 2.2 is greater distally from the steps 2.3 than proximally. The carrier 7 can be moved until proximally abutting this step 2.3 without being deformed or with only a small extent of deformation. In order to move proximally beyond the step 2.3 the collar 7.2 of the carrier 7 must be deformed more. The force required for deforming the collar 7.2 is defined by the resilience of the collar 7.2 and by the geometry of the collar 7.2 and the body ribs 2.2.

Referring again to FIG. 1A, the syringe barrel 8.2 is arranged as a hollow cylinder defining a cavity 8.3 for receiving a drug. A hollow injection needle 9 is arranged at a distal end of the syringe barrel 8.2 in a manner to be in fluid communication with the cavity 8.3. A stopper 10 is disposed within the syringe barrel 8.2 for proximally limiting the cavity 8.3. The stopper 10 may be displaced within the syringe barrel 8.2 for ejecting the drug from the cavity through the needle 9.

A piston rod 11 is arranged within the body 2 in a manner to engage the stopper 10 for displacing it within the syringe barrel 8.2. In an exemplary embodiment the piston rod 11 is attached to the body 2 preventing relative movement between the piston rod 11 and the body 2. In the illustrated embodiment the piston rod 11 is integrally shaped with the body 2. In another exemplary embodiment the piston rod 11 may be secured to the body 2, e.g., by latches.

A sleeve spring 12 is arranged between the carrier 7 and the longitudinal ribs 6.2 in the sleeve 6 in a manner biasing the sleeve 6 in the distal direction D relative to the carrier 7 such that the collar 6.1 of the sleeve 6 abuts an axial stop 2.1 in the body 2, whereas the collar 7.2 of the carrier 7 abuts the step 2.3 in the body 2. The carrier 7 is hence in an initial position IP relative to the body 2.

In order to perform an injection, the medicament delivery device 1 may be operated according to the following exemplary method.

If applicable, a protective needle sheath is removed from the needle 9.

Figure 2:
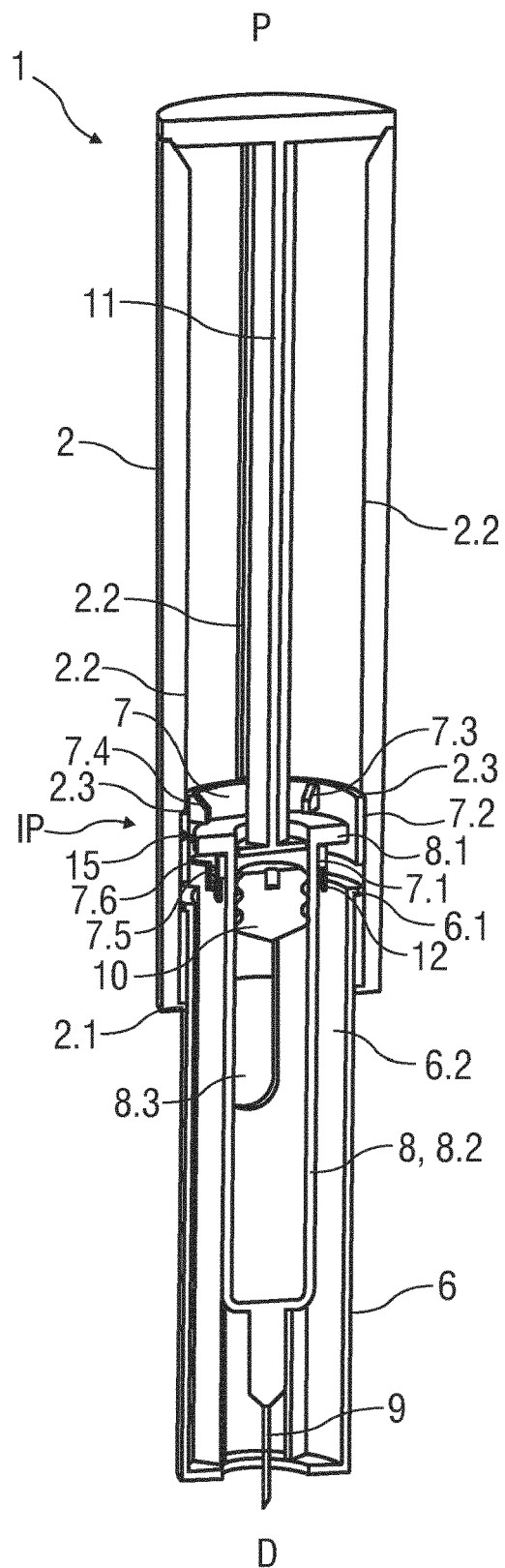
FIG. 2 is a schematic view of an exemplary embodiment of a medicament delivery device according to the present invention during use.

The needle 9 is located within the sleeve 6 preventing a user from touching and seeing it. In this state the medicament delivery device 1 may be held at the body 2 and the sleeve 6 may be pushed against an injection site, e.g. a patient's skin. Consequently the sleeve 6 moves in the proximal direction P relative to the body 2 against the force of the sleeve spring 12. FIG. 2 is a schematic view of the medicament delivery device 1 with the sleeve 6 moved in the proximal direction P within the body 2 and the carrier 7 in the initial position. FIG. 3 is a corresponding cross sectional view. Due to the movement of the sleeve 6 in the proximal direction P, the sleeve spring 12 is compressed between the sleeve 6 and the carrier 7. The carrier 7 remains in position as it is stopped by the step 2.3 in the body 2. The resistance of the material of the carrier 7 opposing deformation for disengaging the step 2.3 provides the counterforce against the force of the sleeve spring 12 to hold the carrier 7 in position.

Consequently, the syringe 8 and the needle 9 stay in position relative to the body 2 while the sleeve 6 moves in the proximal direction P and the needle 9 is hence exposed and inserted into the injection site. Once the sleeve spring 12 is fully compressed or if the sleeve 6 abuts the carrier 7, movement of the sleeve 6 relative to the carrier 7, syringe 8 and needle 9 stops. The needle 9 has reached its insertion depth. Any further movement of the sleeve 6 relative to the body 2 in the proximal direction P hence increases the force on the carrier 7 deforming it in such a manner that the collar 7.2 overcomes the step 2.3 and starts moving with the syringe 8 out of the initial position IP relative to the body 2.

The deformation of the carrier 7 may be achieved as follows:

The inner collar 7.5 is moved in the proximal direction P by the sleeve 6 and the at least nearly completely compressed sleeve spring 12 which acts between the sleeve 6 and the inner collar 7.5. At the same time, the collar 7.2 is still abutted against the step 2.3 and does not move. The connecting ribs 7.6 attached on first sections 7.7 on the distal edge of the collar 7.2 pull the distal edge of the first sections 7.7 inwards thereby tilting the first sections 7.7 such that their proximal edges deflect radially outwards. As the overall circumference of the collar 7.2 remains substantially constant this tilting causes a tilting in an opposite direction in second sections 7.8 of the collar 7.2 between the first sections 7.7 which consequently disengage the step 2.3 allowing the collar 7.2 to move along the ribs 2.2.

Figure 4:
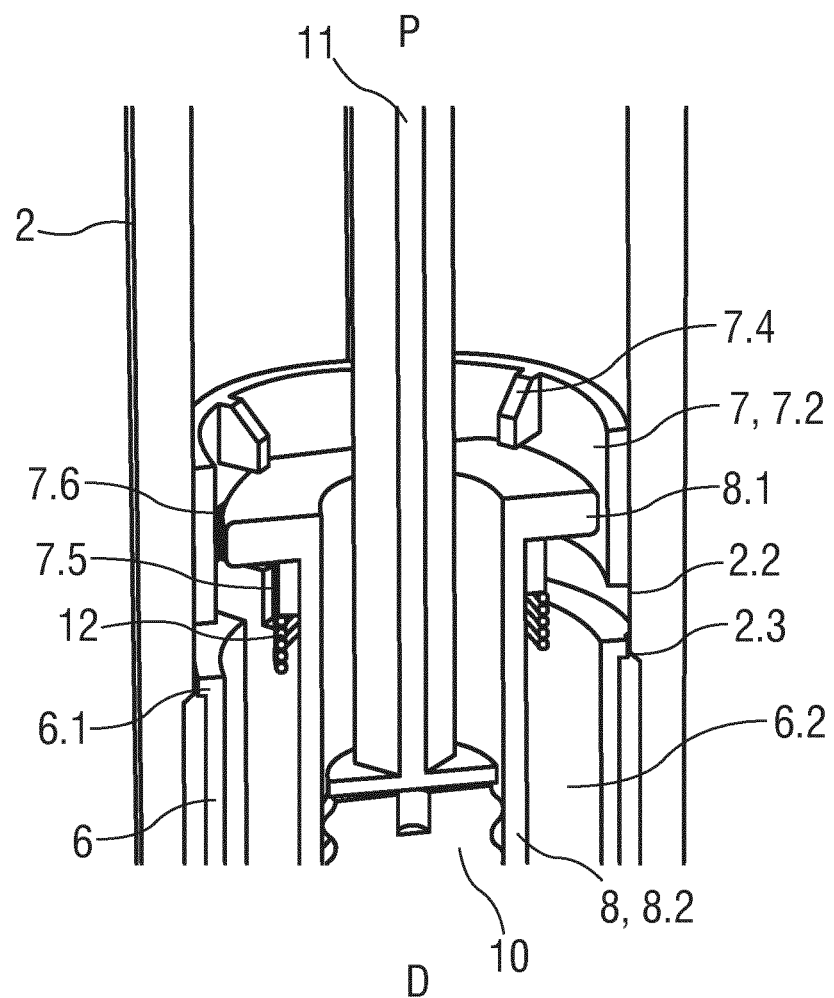
FIG. 4 is a perspective detail view of an exemplary embodiment of a medicament delivery device according to the present invention during use.
Figure 5:
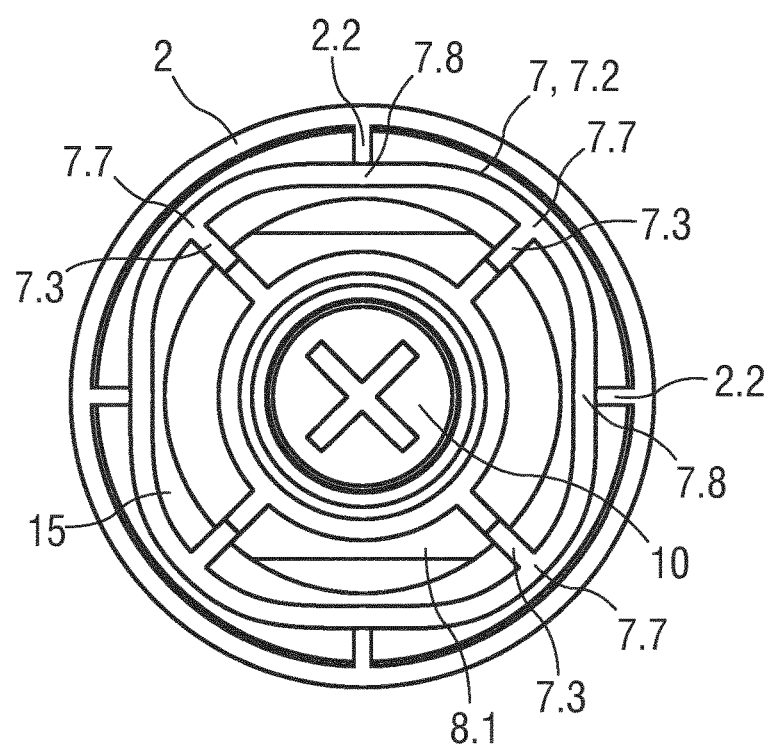
FIG. 5 is a schematic cross sectional view of an exemplary embodiment of a medicament delivery device according to the present invention.

FIG. 4 is a perspective detail view of the medicament delivery device 1 with the carrier 7 moved proximally beyond the initial position IP. FIG. 5 is a corresponding cross sectional view.

As the piston rod 11 is coupled to the body 2 the movement of the carrier 7 relative to the body 2 causes the piston rod 11 to abut the stopper 10 and displace it within the syringe barrel 8.2 ejecting the drug from the cavity 8.3 through the injection needle 9 into the injection site.

As the carrier 7 moves within the body 2 the controlled distortion of the collar 7.2 by the body ribs 2.2 provides an additional force opposing the delivery of the drug from the cavity 8.3. This force can thus be adjusted by the resilience of the carrier 7 and by the geometry of the body ribs 2.2 and the carrier 7.

In the illustrated embodiments the resilient carrier 7 is applied in a medicament delivery device 1 with manual needle insertion and manual drug delivery. Likewise, the resilient carrier 7 could be applied in an automatic medicament delivery device with automatic needle insertion and/or automatic drug delivery in order to adjust the injection force. In this case the resilient carrier 7 could be arranged to interact with the piston rod 11 for opposing the injection force, wherein the piston rod 11 would not necessarily have to be attached to the body 2.

Figure 6:
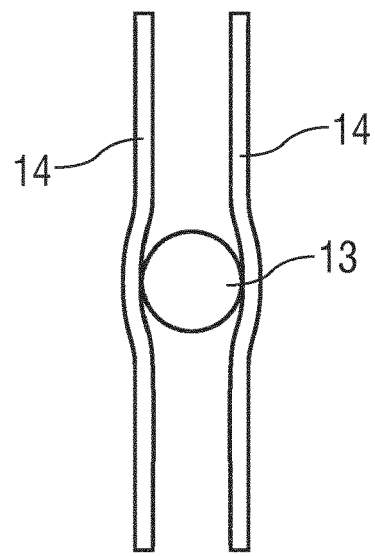
FIG. 6 is a schematic view of an exemplary embodiment of two flexible ribs engaged to a pin.

FIG. 6 is a schematic view of an exemplary embodiment of an application of flexible material to oppose and control a relative movement between two components. A pin 13 on one of the components, e.g. the body 2 or the carrier 7, may be arranged between two resilient ribs 14 on the other one of the components. The distance between the ribs 14 in the relaxed state is smaller than the diameter of the pin 13. If the pin 13 is moved relative to the ribs 14 it has to overcome the resilience of the ribs 14 and splay them apart.

Figure 7:
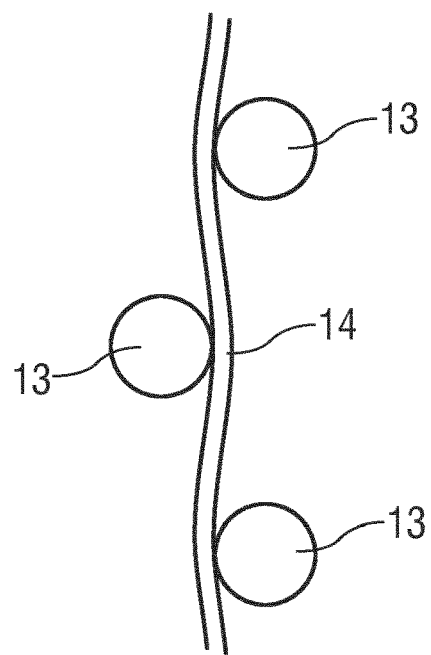
FIG. 7 is a schematic view of an exemplary embodiment of a flexible rib engaged to a plurality of pins.

FIG. 7 is a schematic view of an exemplary embodiment of an application of flexible material to oppose a relative movement between two components. A resilient rib 14 on one of the components, e.g. the body 2 or the carrier 7, may be arranged between successive pins 13 on the other one of the components such that the rib 14 is staggered by the pins 13. If the pins 13 are moved relative to the rib they have to overcome the resilience of the rib 14 and change its deformation.

In an exemplary embodiment a cap may be arrangeable over a distal end of the medicament delivery device 1. In an exemplary embodiment a viewing window may be arranged in the cap allowing viewing a syringe arrangeable within the medicament delivery device 1.

The sleeve 6 may comprise one or more lateral sleeve windows adapted to axially align with the viewing windows in the cap in an initial state thus allowing inspection of the syringe contents.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device, comprising:
   a piston rod,
   a container carrier configured to retain a medicament container within a body,
   wherein at least one longitudinal rib associated with the piston rod is arranged to engage the carrier, wherein at least the container carrier comprises a resilient material adapted to be deformed by an engagement between the container carrier and the at least one longitudinal rib,
   wherein the container carrier is arranged within the body, wherein the piston rod is connected to the body and wherein the at least one longitudinal rib is arranged within the body in a manner to protrude in a radial inward direction,
   further comprising a sleeve configured to move within the body along a longitudinal axis such that movement of the sleeve covers or exposes an injection needle,
   wherein the at least one longitudinal rib comprises a step, a portion of the at least one longitudinal rib, proximal to the step, being configured to deform the carrier to a greater extent than a portion of the at least one longitudinal rib, distal to the step.

2. The medicament delivery device according to claim 1, wherein the at least one longitudinal rib comprises a resilient material adapted to be deformed by the engagement between the container carrier and the at least one longitudinal rib.

3. The medicament delivery device according to claim 1, wherein the container carrier is movable from an initial position in a proximal direction relative to the body.

4. The medicament delivery device according to claim 1, wherein the medicament container comprises a syringe, wherein the container carrier comprises a transverse portion adapted to support a flange on a syringe barrel of the syringe such that the syringe is prevented from moving in a distal direction relative to the carrier, and wherein the transverse portion is attached to a ring shaped collar adapted to engage the at least one longitudinal rib.

5. The medicament delivery device according to claim 4, wherein the collar has a substantially circular cross section when relaxed, and wherein an internal diameter of the collar is greater than a maximum external diameter of the flange of the syringe.

6. The medicament delivery device according to claim 4, wherein the transverse portion comprises an inner collar connected to first sections of the collar by a plurality of connecting ribs.

7. The medicament delivery device according to claim 6, wherein the inner collar has an internal diameter substantially corresponding to an external diameter of the syringe barrel.

8. The medicament delivery device according to claim 6, wherein on axial movement of the collar relative to the inner collar the connecting ribs are adapted to tilt the first sections with respect to the longitudinal axis.

9. The medicament delivery device according to claim 4, wherein one or more carrier ribs are arranged on an inner surface of the collar and protrude in a radial inward direction, and the one or more carrier ribs are configured to engage the flange on the syringe barrel and restrict movement of the syringe in a proximal direction relative to the carrier.

10. The medicament delivery device according to claim 9, wherein the one or more carrier ribs comprise a proximal ramp.

11. The medicament delivery device according to claim 1, wherein the at least one longitudinal rib comprises the step adapted to allow proximal movement of the carrier without deformation until the carrier proximally abuts the step.

12. The medicament delivery device according to claim 1, wherein a sleeve spring is arranged between the carrier and the sleeve in a manner biasing the sleeve in a distal direction relative to the carrier.

13. The medicament delivery device according to claim 1, wherein the medicament container comprises a syringe.

14. The medicament delivery device according to claim 1, wherein the medicament container comprises a pharmaceutically active compound.

15. A method comprising:
placing an end of a sleeve of a medicament delivery device against a target surface;
applying a force to the medicament delivery device in a direction towards the target surface, the force moving the sleeve in a proximal direction relative to a body of the medicament delivery device and compressing a sleeve spring against a carrier retained by a step on an inner surface of the body, the proximal movement of the sleeve exposing a needle of a syringe such that the force inserts the needle into the target surface; and
continuing to apply the force to the medicament delivery device, the force detaching the carrier by deforming a portion of the carrier away from the inner surface, and driving the deformed carrier proximally such that a piston rod expels a medicament from a syringe into the needle.

16. A medicament delivery device, comprising:
a piston rod,
a container carrier configured to retain a medicament container within a body, and
a sleeve configured to move within the body along a longitudinal axis such that movement of the sleeve covers or exposes an injection needle,
wherein at least one longitudinal rib associated with the piston rod is arranged to engage the carrier,
wherein the container carrier comprises a resilient material adapted to be deformed by an engagement between the container carrier and the at least one longitudinal rib,
wherein the container carrier is arranged within the body,
wherein the piston rod is connected to the body,
wherein the at least one longitudinal rib is arranged within the body in a manner to protrude in a radial inward direction,
wherein the container comprises a syringe, wherein the container carrier comprises a transverse portion adapted to support a flange on a syringe barrel of the syringe such that the syringe is prevented from moving in a distal direction relative to the carrier, and wherein the transverse portion is attached to a ring shaped collar adapted to engage the at least one longitudinal rib, and
wherein one or more carrier ribs are arranged on an inner surface of the collar and protrude in a radial inward direction, the one or more carrier ribs are configured to engage the flange on the syringe barrel and restrict movement of the syringe in a proximal direction relative to the carrier.

17. The medicament delivery device according to claim 16, wherein the at least one longitudinal rib comprises a resilient material adapted to be deformed by the engagement between the container carrier and the at least one longitudinal rib.

18. The medicament delivery device according to claim 16, wherein the container carrier is movable from an initial position in a proximal direction relative to the body.

19. The medicament delivery device according to claim 16, wherein the medicament container comprises a syringe.

20. The medicament delivery device according to claim 16, wherein the medicament container comprises a pharmaceutically active compound.

* * * * *